United States Patent [19]
Winger et al.

[11] Patent Number: 5,853,990
[45] Date of Patent: Dec. 29, 1998

[54] REAL TIME HOMOGENEOUS NUCLEOTIDE ASSAY

[75] Inventors: Edward E. Winger, 470A Cola Ballena, Alameda, Calif. 94501; Donald J. Kessler, Redwood Shores; David E. Hargrove, Livermore, both of Calif.

[73] Assignee: Edward E. Winger, Alameda, Calif.

[21] Appl. No.: 687,662

[22] Filed: Jul. 26, 1996

[51] Int. Cl.⁶ .............. C12Q 1/68; C12P 19/34; C07H 21/04; C07H 21/00
[52] U.S. Cl. ................ 435/6; 435/6; 435/91.2; 536/24.3; 536/25.32
[58] Field of Search ............ 435/6, 91.2; 536/24.3, 536/25.32

[56] References Cited

U.S. PATENT DOCUMENTS

| | | | |
|---|---|---|---|
| 3,996,345 | 12/1976 | Ullman et al. | 424/12 |
| 3,998,943 | 12/1976 | Ullman | 424/12 |
| 4,160,016 | 7/1979 | Ullman | 424/8 |
| 4,174,384 | 11/1979 | Ullman et al. | 424/8 |
| 4,199,559 | 4/1980 | Ullman et al. | 424/8 |
| 4,683,194 | 7/1987 | Saiki et al. | 435/6 |
| 4,683,202 | 7/1987 | Mullis | 435/91 |
| 4,800,159 | 1/1989 | Mullis et al. | 435/172.3 |
| 4,876,187 | 10/1989 | Duck et al. | 435/6 |
| 4,889,818 | 12/1989 | Gelfand et al. | 435/194 |
| 4,914,210 | 4/1990 | Levenson et al. | 548/413 |
| 5,011,769 | 4/1991 | Duck et al. | 435/6 |
| 5,210,015 | 5/1993 | Gelfand et al. | 435/6 |
| 5,244,797 | 9/1993 | Kotewicz et al. | 435/194 |
| 5,487,972 | 1/1996 | Gelfand et al. | 435/6 |

FOREIGN PATENT DOCUMENTS 0 070 685  10/1985  European Pat. Off. .

OTHER PUBLICATIONS

Mullis and Faloona, *Methods in Enzymol.*, vol. 155, p. 335 (1987).
Livak et al., *PCR Methods and Applications,* 4:357 (1995).
Duck et al., *Bio Techniques,* 9;142 (1990).
Bekkaoui et al., *Bio Techniques,* 20:240 (1996).

*Primary Examiner*—Kenneth R. Horlick
*Assistant Examiner*—Joyce Tung
*Attorney, Agent, or Firm*—Nathan P. Koenig; Crosby, Heafey, Roach & May

[57] ABSTRACT

A method for performing real time, homogeneous assay of a target nucleic acid comprising annealing a labeled, ribo-oligonucleotide probe to the target DNA sequence and degrading a portion of the probe with RNase H to release labeled fragments. Sequential measurements of the released fragments permits kinetic characterization of the presence of the target sequence. Preferably, the assay is integrated into a polymerase chain reaction so that target amplification can be detected in real time.

7 Claims, 1 Drawing Sheet

REAL TIME HOMOGENEOUS NUCLEOTIDE ASSAY

BACKGROUND OF THE INVENTION

Recent advances in the general field of molecular biology have made it possible to detect specific genes of clinical and commercial importance. The use of nucleic acid hybridization assays as a research tool for the detection and identification of a unique deoxyribonucleic acid (DNA) sequence or a specific gene in a complete DNA, a mixture of DNA's, or a mixture of DNA fragments have made it possible to diagnose human disease at the genetic level.

The most common techniques for detecting a specific gene sequence are hybridization-based assays. A specific nucleotide sequence or probe is marked with a detectable label, typically a radioactive label (isotopic) or chemical modification (non-isotopic). The detectable label is combined with the nucleic acid sample of interest, either in situ as part of intact cells or as isolated DNA or RNA fragments. The hybridization conditions should be those which allow the probe to form a specific hybrid with its complementary DNA or RNA target while not becoming bound to non-complementary DNA or RNA molecules. The target sample sequence can be either free in solution or immobilized on a solid substrate. The probe's detectable label provides a means for determining whether hybridization has occurred and, thus, for detecting the DNA or RNA target.

Detection methods employed in nucleic acid hybridization based assay systems allow for the distinction of hybridized probe to the target nucleic acid sequence from the unhybridized probe. One of the oldest and most widely used procedures is called the Southern blot filter hybridization assay. This assay is carried out by isolation and immobilization of the nucleic acid target to a solid membrane support(nylon, nitrocellulose, etc.). The membrane bound nucleic acid target is subject to denaturation conditions (heating, or alkaline treatment) and subsequently treated with a solution containing a labeled probe and allowed to hybridize under conditions which reinforce the specificity of the labeled probe to its complementary target sequence. Unhybridized labeled probe is then washed away and the hybridized label probe is detected by the means specific for that label type, i.e., isotopic labeled probe detection would utilize x-ray film and autoradiography.

Probes labeled with non-isotopic or chemicals such as a high energy transfer fluorescent moieties and their use and detection in immunofluorescent assays is described in U.S. Pat. Nos. 3,996,345; 3,998,943; 4,160,016; 4,174,384; and 4,199,559, each of which are incorporated in their entirety by reference. These patents pertain to assays which utilize fluorescent light emitted from an irradiated sample and the use of chemical species(quenchers) to absorb some of the light energy.

European Patent Publication No. 70,685 describes the design, detection and use of non-radiative energy transfer probes in a homogeneous nucleic acid diagnostic assay. This technique uses two probes which hybridize to adjacent sequences on the target DNA. A chemiluminescent moiety and an absorber/emitter moiety are attached to the 3' and 5' ends of the probes so that when the probes hybridize, the moieties are brought into close enough proximity to allow for non-radiative energy transfer. Presence of the target DNA allows the probes to hybridize and emit radiation having the wavelength specific to the absorber/emitter moiety.

The recent advances in automated nucleic acid oligonucleotide (ribo- and deoxyribo-) synthesis and the polymerase chain reaction (PCR) method of DNA amplification have increased the power and sensitivity of nucleic acid hybridization assays. The use of automated chemical nucleic acid synthesizers for the synthesis of short gene fragments (DNA and RNA) is well described by Alvarado-Urbina et. al., *Science*, 214:270 (1981). Automated synthesizers have increased the efficiency of incorporating specific moieties into the short gene fragments which can serve as detectable labels and quenchers on probes for the detection and isolation of a desired natural gene from a living organism or a virion. The short gene fragments can also serve as primers in PCR and reverse transcription(RT) assays to enable amplification or copying of the genetic information carried in natural genes.

The PCR method of DNA amplification is well described by Mullis and Faloona, Methods in Enzymol., vol. 155, pg. 335 (1987). Improvements in the PCR technique are disclosed in U.S. Pat. Nos. 4,683,202; 4,683,195; and 4,800,159, each of which are incorporated in their entirety by reference. PCR is an in vitro method for the enzymatic synthesis of specific DNA sequences, using two deoxyoligonucleotide primers that hybridize to opposite strands and flank the specific target region of DNA that is to be amplified. The use of automated thermal cyclers allows a repetitive series of reaction steps involving template denaturation, primer annealing and the extension of the annealed primers by DNA polymerase resulting in the exponential accumulation of the specific target region of DNA whose termini are defined by the 5' end of the primers. Selective enrichment of a specific target region of DNA sequence by a factor of $10^9$ was described by Saiki et. al.,*Science*, 230:1350 (1985).

Reverse transcription is a commonly employed molecular biology technique for the in vitro synthesis of single-stranded complementary DNA(cDNA) from specific RNA sequences for the preparation of cDNA libraries or can be used for the synthesis of first strand cDNA for use in subsequent amplification reactions; i.e., PCR. The use of reverse transcriptase for cDNA synthesis is described by Maniatis, et al., *Molecular Cloning, A Laboratory Manual*, pg. 8.11 (1989). Reverse transcriptase is a protein which extends the 3' end of deoxyoligonucleotide primers annealed to a specific complementary sequence of single-stranded RNA. Modification of the reverse transcriptase enzyme have allowed longer cDNA synthesis and higher yields and are described in U.S. Pat. No. 5,244,797, which is incorporated in its entirety by reference.

The PCR technique alone and in combination with the RT reaction is an extremely powerful method for amplifying nucleic acid sequences, however the detection of the amplified material may require additional manipulation and subsequent handling of the PCR products to determine whether the target region of DNA is present. For example, removal of labeled probe that has not come into contact with the target sequence significantly complicates typical hybridization assays. A more useful probe technique would minimize the number of additional handling steps currently required for the detection of the amplified material. Ideally, such a technique would combine the amplification and detection steps into a homogeneous system, thereby eliminating the need for a post amplification phase separation of target-contacted and target-non-contacted probe prior to signal detection. Such a homogeneous system permits repeated detection of the signal permitting a kinetic analysis of the amplification process.

A kinetic analysis offers significant advantages over a single, end-point analysis. For example, the qualitative assessment of the development of signal can greatly increase the accuracy of amplification systems by revealing problems such as false positives or other false quantifications. However, the design of homogeneous probe systems is constrained by the probe's potential interference with the amplification. In PCR, for example, the processivity of the polymerase must not be blocked by the presence of a down stream probe.

U.S. Pat. Nos. 5,210,015 and 5,487,972, both of which are incorporated in their entirety by reference, describe methods for nucleic acid detection which rely on the 5' to 3' nuclease activity of a nucleic acid polymerase to cleave annealed labeled DNA probes and thus release labeled oligonucleotide fragments for detection. An enhancement on this technique is described by Livak et al., PCR *Methods and Applications*, 4:357 (1995), using a reporter fluorescent dye and a quencher fluorescent dye attached to the 5' and 3' ends of an oligonucleotide probe. As the polymerase moves along the target DNA sequence in a 3' direction, its 5' nuclease activity first displaces and then cleaves the oligonucleotide probe, separating the reporter from the quencher. Thus, presence of target DNA sequence may be measured by detecting fluorescence of the reporter dye.

These assays depend on the 5' nuclease activity of the polymerase which places significant constraints on the design of probes that can be used. For example, the label must be attached to DNA and the probe must be designed to allow cleavage from the 5' end. Moreover, since one enzyme is being required to provide both polymerase and nuclease activity, it is not possible to independently select or optimize those events.

Existing alternatives to PCR based assays rely on amplification of the signal produced by the target sequence, instead of amplifying the target directly. These methods require significant handling steps and are directed to an end point analysis as opposed to a kinetic, real time determination of target sequence presence.

For example, U.S. Pat. Nos. 4,876,187 and 5,011,769, which are incorporated in their entirety by reference, Duck et al., *BioTechniques*, 9:142 (1990) and Bekkaoui et al., *BioTechniques*, 20:240 (1996) disclose a cycling probe method that employs probes comprising RNA, preferably DNA:RNA:DNA chimeras. The reaction is carried out isothermally, using a temperature at which the chimeric probes will anneal to the target DNA. An enzyme such as RNase H is used to digest the RNA portion of the probe and generate shorter, labeled oligonucleotides which dissociate at the reaction temperature. The target DNA sequence is then available for hybridization with another probe and, after a number of cycles, sufficient label has been generated to collect and detect. In general, these methods rely on immobilizing a portion of the label to allow for phase separation and signal recovery and measurement. Bekkaoui et al. report a modification of this technique, dealing with the formation of a RNase-streptavidin fusion enzyme and its use with a biotinylated probe. The streptavidin-biotin binding brings the fusion enzyme into proximity with the probe and thus increases its RNase activity. However, the enzyme becomes non-functional once the attached probe is cleaved, preventing it from participating in subsequent cycles.

The above signal amplification strategies do not generate a real time signal since a number of cycles are required before sufficient label is released to permit detection. Further, the techniques are designed to be used as an alternative to conventional target amplification strategies and require isothermal conditions. However, the methods rely on phase separation for detection of the label, and thus, are not directed to homogenous systems. Also, the choice of probe design is limited because the nuclease activity of polymerases could attack the DNA portion of a chimeric probes, generating false signal.

Accordingly, there remains a need for strategies capable of providing real time homogenous detection of nucleic acid amplification capable of using more versatile probe designs.

SUMMARY OF THE INVENTION

The invention comprises a method for the detection of a target DNA sequence in a sample which includes: a) contacting and annealing a labeled probe to a target single-stranded DNA sequence having a region complementary to the probe; b) cleaving with a ribo-nucleic acid nuclease capable of hydrolyzing ribonucleotides in a double stranded RNA:DNA duplex to release labeled probe fragments; and c) making sequential measurements of the released labeled fragments to permit the kinetic characterization of the target DNA sequence. This assay is carried out homogeneously in one reaction mixture.

Preferably, the assay is used in conjunction with amplification of the target DNA sequence, using PCR for example. In these embodiments, the method comprises a) providing primers containing sequences complementary to regions in the the target DNA sequence, each capable of priming the synthesis of a complementary oligonucleotide, such that the complementary oligonucleotide primed can serve as a template for the synthesis of the complementary oligonucleotide primed by the other; b) providing labeled probe having a sequence complementary to a portion of the target DNA sequence; c) amplifying the target DNA sequence employing a polymerizing agent with the cycling steps of:

i) contacting and annealing the labeled probe to the target DNA sequence, ii) annealing the first and/or second primer(s), iii) cleaving the RNA of the annealed probe with a ribo-nucleic acid nuclease to release labeled ribo-oligonucleotide fragments, iv) extending the primers with the polymerization agent, and v) denaturing the extended primer(s) and the target DNA sequence; and d) making sequential measurements of the release of labeled fragments to permit the kinetic characterization of target DNA sequence amplificiation.

In another preferred embodiment, the method comprises the use of a labeled probe having a reporter fluorescent dye at one terminus and a quencher fluorescent dye at the other terminus and the step of detecting the release of labeled ribo-oligonucleotide fragments comprises measuring reporter fluorescence. The quencher suppresses reporter fluorescence until the annealed probe is cleaved, allowing discrimination between target-contacted probe and target non-contacted probe.

The methods of this invention allow detection of a target DNA sequence in a homogeneous, real time system. When combined with target DNA amplification, the method offers probe release independent of polymerase activity and great flexibility in probe design. Futher, the kinetic detection of this invention allows real time analysis unlike the prior art endpoint assays.

DETAILED DESCRIPTION OF THE INVENTION

Definitions

Figure 1:
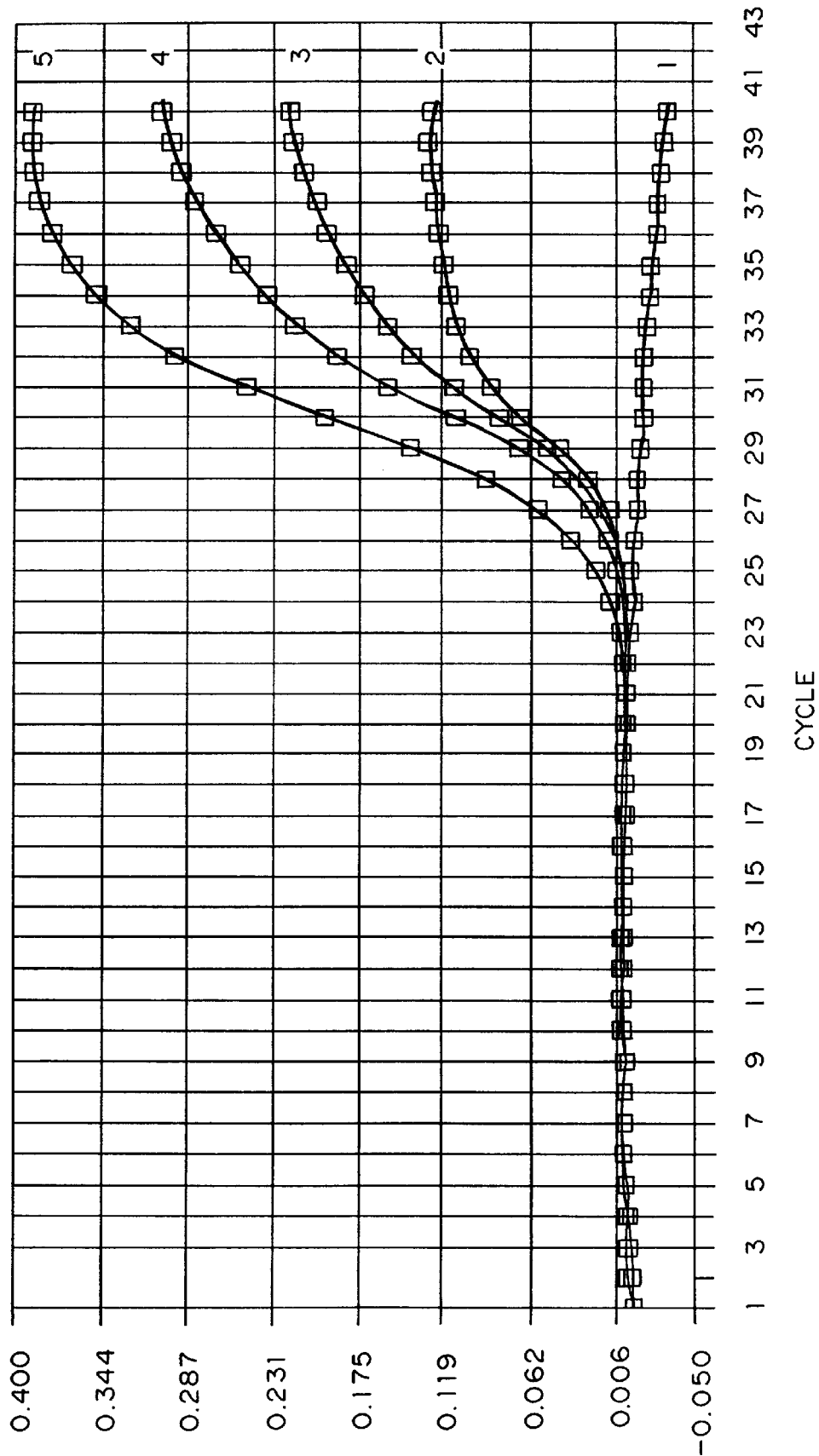
FIG. 1 is a graphical representation of the increase in reporter fluorescence observed as target DNA amplification proceeds in an embodiment of this invention.

The term "sample" or "specimen" refers to nucleic acid isolated from an individual(s) or any nucleic acid containing entity, including but not limited to; skin, plasma, serum, spinal fluid, lymph fluid, synovial fluid, urine, tears, blood cells, organs, tumors, in vitro cell culture constituents, bacteria and viruses.

As used herein, the terms "nucleic acid", "polynucleotide" and "oligonucleotide" refer to primers, probes, oligomer fragments to be detected, oligomer controls and unlabeled blocking oligomers and shall be generic to polydeoxyribonucleotides (containing 2-deoxy-D-ribose), to polyribonucleotides (containing D-ribose) as well as chimeric polynucleotides (containing 2-deoxy-D-ribose and D-ribose nucleotides), and to any other type of polynucleotide which is an N glycoside of a purine or pyrimidine base, or modified purine or pyrimidine bases. There is no conceived distinction in length between the term "nucleic acid","polynucleotide" and "oligonucleotide", and these terms are used interchangeably. Thus, these terms include double-and single stranded DNA, as well as double- and single stranded RNA. The oligonucleotide is composed of a sequence of at least 8 nucleotides, by preference at least 10–12 nucleotides, and more preferably at least 15–20 nucleotides coterminous to a region of the designated nucleotide sequence. "Coterminous" means identical to or complementary to the determined sequence.

The oligonucleotide is not necessarily limited to a physically derived species isolated from any existing or natural sequence but may be generated in any manner, including chemical synthesis, DNA replication, reverse transcription or a combination thereof. The terms "oligonucleotide" or "nucleic acid" refers to a polynucleotide of genomic DNA or RNA, cDNA, semisynthetic, or synthetic origin which, by virtue of its derivation or manipulation: (1) is not affiliated with all or a portion of the polynucleotide with which it is associated in nature; and/or (2) is connected to a polynucleotide other than that to which it is connected in nature; and (3) is unnatural( not found in nature).

Oligonucleotides are composed of reacted mononucleotides to make oligonucleotides in a manner such that the 5' phosphate of one mononucleotide pentose ring is attached to the 3' oxygen of its neighbor in one direction via a phosphodiester linkage, and is referred to as the "5' end" end of an oligonucleotide if its 5' phosphate is not linked to the 3' oxygen of a mononucleotide pentose ring and subsequently referred to as the "3' end" if its 3' oxygen is not linked to a 5' phosphate of a subsequent mononucleotide pentose ring. A nucleic acid sequence, even if internalized to a larger oligonucleotide, also may be said to have 5' and 3' ends. Two distinct, non-overlapping oligonucleotides annealed to two different regions of the same linear complementary nucleic acid sequence, so the 3' end of one oligonucleotide points toward the 5' end of the other, will be termed the "upstream" oligonucleotide and the latter the "downstream" oligonucleotide. In general, "downstream" refers to a position located in the 3' direction on a single stranded oligonucleotide, or in a double stranded oligonucleotide, refers to a position located in the 3' direction of the reference nucleotide strand.

The term "primer" may refer to more than one oligonucleotide, whether isolated naturally, as in a purified restriction digest, or produced synthetically. The primer must be capable of acting as a point of initiation of synthesis along a complementary strand (DNA or RNA) when placed under reaction conditions in which the primer extension product synthesized is complementary to the nucleic acid strand. These reaction conditions include the presence of the four different deoxyribonucleotide triphosphates and a polymerization-inducing agent such as DNA polymerase or reverse transcriptase. The reaction conditions incorporate the use of a compatible buffer (including components which are cofactors, or which affect pH, ionic strength, etc.), at an optimal temperature. The primer is preferably single-stranded for maximum efficiency in the amplification reaction.

A complementary nucleic acid sequence refers to an oligonucleotide which, when aligned with the nucleic acid sequence such that the 5' end of one sequence is paired with the 3' end of the other. This association is termed as "antiparallel." Modified base analogues not commonly found in natural nucleic acids may be incorporated ( enzymatically or synthetically) in the nucleic acids including but not limited to primers, probes or extension products of the present invention and may include, for example, inosine and 7-deazaguanine. Complementarity of two nucleic acid strands may not be perfect; some stable duplexes may contain mismatched base pairs or unmatched bases and one skilled in the art of nucleic acid technology can determine their stability hypothetically by considering a number of variables including, the length of the oligonucleotide, the concentration of cytosine and guanine bases in the oligonucleotide, ionic strength, pH and the number, frequency and location of the mismatched base pairs. The stability of a nucleic acid duplex is measured by the melting or dissociation temperature, or "Tm." The Tm of a particular nucleic acid duplex under specified reaction conditions. It is the temperature at which half of the base pairs have disassociated.

As used herein, the term "target sequence" or "target nucleic acid sequence" refers to a region of the oligonucleotide which is to be either amplified, detected or both. The target sequence resides between the two primer sequences used for amplification or as a reverse transcribed single-stranded cDNA product. The target sequence may be either naturally derived from a sample or specimen or synthetically produced.

As used herein, a "probe" comprises a ribo-oligonucleotide which forms a duplex structure with a sequence in the target nucleic acid, due to complementarity of at least one sequence of the ribo-oligonucleotide to a sequence in the target region. The probe, preferably, does not contain a sequence complementary to the sequence(s) used to prime the polymerase chain reaction (PCR) or the reverse transcription (RT) reaction. The probe may be chimeric, that is, composed in part of DNA. Where chimeric probes are used, the 3' end of the probe is generally blocked if this end is composed of a DNA portion to prevent incorporation of the probe into primer extension product. The addition of chemical moieties such as biotin, fluorescein, rhodamine and even a phosphate group on the 3' hydroxyl of the last deoxyribonucleotide base can serve as 3' end blocking groups and under specific defined cases may simultaneously serve as detectable labels or as quenchers. Furthermore, the probe may incorporate modified bases or modified linkages to permit greater control of hybridization, polymerization or hydrolyzation.

The term "label" refers to any atom or molecule which can be used to provide a detectable (preferably quantifiable) real time signal. The detectable label can be attached to a nucleic acid probe or protein. Labels provide signals detectable by either fluorescence, phosphorescence, chemiluminescence, radioactivity, colorimetric (ELISA), X-ray diffraction or absorption, magnetism, enzymatic activity, or a combination of these.

The term "absorber/emitter moiety" refers to a compound that is capable of absorbing light energy of one wavelength while simultaneously emitting light energy of another wavelength. This includes phosphorescent and fluorescent moieties. The requirements for choosing absorber/emitter pairs are: (1) they should be easily functionalized and coupled to the probe; (2) the absorber/emitter pairs should in no way impede the hybridization of the functionalized probe to its complementary nucleic acid target sequence; (3) the final emission (fluorescence) should be maximally sufficient and last long enough to be detected and measured by one skilled in the art; and (4) the use of compatible quenchers should allow sufficient nullification of any further emissions.

As used in this application, "real time" refers to detection of the kinetic production of signal, comprising taking a plurality of readings in order to characterize the signal over a period of time. For example, a real time measurement can comprise the determination of the rate of increase of detectable product. Alternatively, a real time measurement may comprise the determination of time required before the target sequence has been amplified to a detectable level.

The term "chemiluminescent and bioluminescent" include moieties which participate in light emitting reactions. Chemiluminescent moieties (catalyst) include peroxidase, bacterial luciferase, firefly luciferase, functionlized iron-porphyrin derivatives and others.

As defined herein, "nuclease activity" refers to that activity of a template-specific ribo-nucleic acid nuclease, RNase H. As used herein, the term "RNase H" refers to an enzyme which specifically degrades the RNA portion of DNA/RNA hybrids. The enzyme does not cleave single or double-stranded DNA or RNA and a thermostable hybrid is available which remains active at the temperatures typically encountered during PCR. Generally, the enzyme will initiate nuclease activity whereby ribo-nucleotides are removed or the ribo-oligonucleotide is cleaved in the RNA-DNA duplex formed when the probe anneals to the target DNA sequence.

As used herein, the term "thermostable nucleic acid polymerase" refers to an enzyme which is relatively stable to heat when compared, for example, to nucleotide polymerases from E. coli and which catalyzes the polymerization of nucleosides. Generally, the enzyme will initiate synthesis at the 3'-end of the primer annealed to the target sequence, and will proceed in the 5'-direction along the template.

The term "hybridization or reaction conditions" refers to assay buffer conditions which allow selective hybridization of the labeled probe to its complementary target nucleic acid sequence. These conditions are such that specific hybridization of the probe to the target nucleic acid sequence is optimized while simultaneously allowing for but not limited to amplification of the target nucleic acid in a PCR assay. The reaction conditions are optimized for co-factors, ionic strength, pH and temperature.

General Method

The practice of this invention will engage, unless otherwise indicated, standard techniques of molecular biology, microbiology and recombinant DNA techniques, which are within the skill of the art.

The various conditions of the invention exploit a property of RNase H. RNase H is an enzyme known to degrade the RNA moiety of RNA-DNA hybrid molecules. RNA:DNA duplexes are a substrate for RNase H due to the particular secondary structure. Thus, RNase is active along the length of the RNA:DNA duplex without positional restriction and thus is not limited to either terminus. RNase H will cleave monoribonucleotides or small ribo-oligonucleotide fragments from the duplex which are destabilized to the point that they dissociate from the larger, complementary polynucleotide (DNA). Thus, cleavage does not depend on the characteristics of the 5' end. This property allows great flexibility in the design of suitable probes.

The present invention exploits the ribonuclease activity of the RNase H when used alone or in conjunction with PCR. This present invention differs from previously described PCR amplification wherein the post-PCR amplified target nucleic acid sequence(s) are detected, for example, by hybridization to a probe which forms a stable duplex with that of the target sequence under stringent hybridization and wash conditions. In contrast to those known detection methods used in post-PCR amplifications, the present invention permits the detection of the target nucleic acid sequences during amplification of the target nucleic acid sequence. In the present invention, a labeled probe is added simultaneously with the PCR primers and RNase H at the start of PCR. The reaction conditions utilized allow for the labeled probe to hybridize to the target nucleic acid sequence which permits the activity of the RNase H to cleave and dissociate the labeled probe fragments prior to the annealing of the PCR primers and the extension activity of the DNA polymerase. The signal generated from hydrolysis (cleavage) and release of the labeled ribo-nucleotide(s) fragments of the probe provides a means for detection of the target nucleic acid sequence during its amplification.

The methods of this invention are also easily adaptable to other nucleic acid amplification systems. For example, homogenous assays of self-sustained sequence replication (3SR) and ligase chain reaction (LCR) systems are within the scope of this invention.

In the present invention, a label is attached to the probe so that the cleaved monoribonucleotides or small ribo-oligonucleotides which are generated by the nuclease activity of the RNase H can be detected. Several strategies may be employed to distinguish the uncleaved labeled ribo- or chimeric oligonucleotide probes from the cleaved labeled probe fragments. This feature of the present invention allows identification of those nucleic acid containing samples or specimens which contain sequences complementary to the ribo- or chimeric oligonucleotide probe.

In the present invention, a sample or specimen is provided which is suspected of containing the particular "target nucleic acid" sequence of interest. The target nucleic acid contained in the sample may be first reverse transcribed (RT) into cDNA, if isolated as single-stranded RNA or it may be isolated as double-stranded genomic DNA. The cDNA or genomic DNA is then denatured, using any suitable denaturing method, including physical, chemical, or enzymatic means, which are known to those skilled in the art. Physical means for strand separation involves heating the nucleic acid until it is completely denatured. Typical heat denaturation involves the use of temperatures between 80° C. and 100° C., for 3 to 10 minutes. The target nucleic acid may exist in a single-stranded form in the sample, such as, for example, single stranded RNA or DNA viruses and only moderate heating may be necessary to alleviate secondary fold back structures.

The denatured nucleic acid strand(s) are then incubated with preselected oligonucleotide primers and a probe under hybridization or reaction conditions which enable the binding of the primers and probe(s) to the single nucleic acid strands. The primers are selected so that their relative positions along a duplex sequence are such that an extension product produced from one primer serves as a template for the extension of the other primer to yield a replicate chain of defined length, when the extension product is separated from its template (complement) under subsequent denaturation conditions.

Because the complementary nucleic acid strands synthesized are longer than either the probe or primer, the strands have more points of contact and thus a greater chance of finding each other over any given period of time. To prevent reannealing of the longer template, a high molar excess of probe and primer(s) are employed to help sway the hybridization kinetics toward primer and probe annealing rather than template reannealing.

The primer(s) length must be adequate to prime the synthesis of extension products in the presence of the reaction conditions. The length and composition of the primer is dependent on many factors, including temperature of the reaction, composition of the primer, the position of the probe annealing site to the primer annealing site, and the ratio of primer to probe concentration. Depending on the complexity of the target sequence, the oligonucleotide primer(s) typically contains about 15–30 nucleotides, although it may contain more or fewer nucleotides. The primers must be sufficiently complementary to selectively anneal to their respective strands and form stable duplexes. The primers used are selected to be completely complementary to the different strands of each specific sequence to be amplified. One skilled in the art may select or design primers which have non-complement sequences the 5' end, such as restriction enzyme digestion sequences, although the 3' end must maintain its complementarity to insure proper extension and amplification by the DNA polymerase.

In the practice of this invention, the labeled probe must be first annealed to its complementary nucleic acid target before the primers anneal. The activity of the RNase H must supersede the DNA polymerase activity, allowing the cleaved probe fragments to dissociate from the nucleic acid target, as to not interfere with the primer extension and amplification of the nucleic acid target region.

To ensure that the labeled probe will anneal to its complementary nucleic acid before primer extension polymerization reaches this duplex region, a variety of techniques may be employed. The invention allows for significant optimization of this characteristic as opposed to the prior art systems limited to DNA oligonucleotide probes. RNA:DNA hybrids are known to have a higher melting temperature than DNA:DNA or chimeric:DNA hybrids of the same base composition permitting greater specificity. The length of complementary nucleic acids is also known to effect the hybridization rate and the relative stability of the duplexes. Shorter nucleic acid molecules generally require a cooler temperature to form sufficiently stable hybrid complexes with the target nucleic acid. Therefore, the probe can be designed to be longer than the primer so that the labeled probe anneals preferentially to the target at higher temperatures relative to primer annealing. Furthermore, the addition of a denaturation solution such as formamide allows for an optimal temperature for the association of RNA:DNA hybrids as compared to DNA:DNA hybrids.

One can also vary the base composition of the primers and the probe to affect thermal stability. For example, the nucleotide composition of the probes can be chosen to have greater G/C content and, consequently, greater thermal stability than the primer(s). One skilled in the art can then utilize the thermocycling parameters to take advantage of the differential thermal stability of the labeled probe(s) and primer(s). Following the denaturation step in thermocycling, one could employ an intermediate temperature which is permissible for probe annealing and RNase H cleavage but not primer binding, and then the temperature can be further reduced to permit primer annealing and extension by the DNA polymerase.

In certain embodiments, it may be desirable to provide a second probe complementary to a different target sequence. Such a probe should have a label that generates an independently detectable signal. The probes may be designed to have different but compatible melting temperatures based on these techniques.

To ensure binding of the labeled oligonucleotide before the primer, a high molar excess of labeled ribo- or chimeric oligonucleotide probe to primer concentration can also be used. Such probe concentrations range from about 5 to 25 times higher than the respective primer concentration, which is generally $0.5–5\times10^7$M.

The oligonucleotide primers and labeled probes may be prepared by a number of methods. Methods for preparing oligonucleotides (deoxy-, ribo, and chimeric) of a specific sequence are known in the art, and include, for example, cloning and restriction of appropriate sequences, direct automated chemical syntheses and enzymatically. Such techniques include, for example, the phosphotriester method, the phosphodiester method, the diethylphosphoramidate method, and the solid support method.

The composition of the probes can be designed to inhibit nuclease activity. The incorporation of modified phosphodiester linkages (e.g., methyl phosphorylthioate or methylphosphonates) in the labeled probe during chemical synthesis may be used to prevent cleavage at a selected site. Depending on the length of the probe, the composition of its 5' complementary region, and the position of the label, one can design a probe to preferentially favor the generation of short or long labeled probe fragments for use in the practice of the invention. Great flexibility in the modification of the probes of this invention is possible so long as a 4–6 base pair RNA:DNA sequence is available as a substrate for RNase H.

The probe is labeled, as described below, by incorporating moieties detectable by spectroscopic, photochemical, biochemical, immunochemical, enzymatic or chemical means. The method of linking or conjugating the label to the probe depends, of course, on the type of label(s) used and the position of the label on the probe, but in general comprises any suitable means of attachment known in the art. Further, the label may be considered attached to a particular nucleotide even though the attachment may comprise one or more intervening nucleotides.

A number of detectable labels which would be suitable for use in this invention, as well as methods for their incorporation into the probe, are known in the art and include, but are not limited to, enzymes (e.g., alkaline phosphatase and horseradish peroxidase) and enzyme substrates, radioactive atoms, fluorescent dyes, chromophores, chemiluminescent/bioluminescent labels, electrochemiluminescent labels, labeled receptor-ligand binding, labeled antibody-antigen coupling, or any other labels that may interact with each other to enhance, alter, or diminish a detectable signal in real time. Should the PCR be practiced using a thermo-cycler instrument, the label must be able to survive the high temperature cycling required in this automated process.

Preferably, two interactive labels may be used on a single probe while maintaining an appropriate spacing of the labels on the probe to permit the separation of the labels during cleavage with the RNase H. In some instances it may be desirable to use a single probe having two different label moieties.

In a preferred embodiment, the interactive labels comprise a reporter (such as a fluoroscein) and quencher (such as a rhodamine) fluorescent dye pair. Each dye is attached to the probe, separated by at least a 4–6 base sequence to provide an adequate substrate for RNase H. In its single stranded state, the probe has sufficient flexibility that the rhodamine comes into proximity with the fluorescein with enough frequency to quench the reporter. However, when the probe anneals to the target nucleic acid sequence and is digested by RNase H, the fluoroscein is separated from the rhodamine, increasing the detectable reporter fluorescence. The fluorescence may be measured in any suitable way, including the Taq-Man LS-50B System (Perkin-Elmer).

A number of modifications may be made to the probe to maximize quenching prior to hybridization and release. For example, the reporter and quencher may be separated by about 10 nucleotides or less so that quenching occurs without depending upon the flexibility of the single stranded probe. In general, the dyes may be attached either at the termini or internally, to optimize detection characteristics. Alternatively, the probe can be designed so that it forms a secondary structure, such as a hairpin, that brings the reporter and quencher into proximity when unhybridized. The use of ribo-oligonucleotides may be used to great advantage in this embodiment. RNA forms inherently more stable secondary structures than DNA or chimeric oligonucleotides. Accordingly, probes can be designed which very efficiently quench reporter fluorescence prior to hybridization leading to assay systems with very low background noise. Additionally, this technique may not be possible using conventional homogeneous assay systems because the DNA:DNA hairpin could be a substrate for the nuclease, leading to false release of label.

In similar, embodiment, detection of the cleaved labeled probe can be achieved using fluorescence polarization. This technique is able to distinguish between large and small molecules based on molecular tumbling. Large molecules ( e.g., intact labeled probe) tumble in solution much more slowly than small molecules. Upon linkage of a fluorescent moiety to the molecule of interest, this fluorescent moiety can be measured (and differentiated) based on molecular tumbling, thus differentiating between intact and digested probe. Detection may be measured during PCR using the ABI Prism 7700 Sequence Detector (Perkin Elmer).

In another embodiment, two labeled ribo- or chimeric oligonucleotide probes are used, each complementary to separate regions of a double-stranded target region, but not to each other. For example, the presence of two probes can potentially double the intensity of the signal generated from a single label and may further serve to reduce product strand reannealing, as often occurs during PCR amplification.

In yet other embodiments, the use of radioactive atoms, such as $^{32}P$, may be suitable for labeling and detection. Enzymatic methods for introducing $^{32}P$ into nucleic acids are known in the art, and include, for example, 5' end labeling with polynucleotide kinase, or random insertion by nick translation and the Klenow fragment. Labels at the 3' terminus may employ polynucleotide terminal transferase to add the desired moiety, such as for example, cordycepin $^{35}S$-dATP, and biotinylated dUTP. The labels may be attached to the ribo- or chimeric oligonucleotide probe directly or indirectly by a variety of techniques. Depending on the precise type of label used, the label might be located at the 5' or 3' end of the probe, located internally in the probe's nucleotide sequence, or attached to carbon spacer arms of various sizes and compositions to facilitate signal interactions. Using commercially available phosphoramidite reagents, one can produce oligomers containing functional groups (e.g., thiols or primary amines) at either terminus via an appropriately protected phosphoramidite. Enzymes can be detected by their activity on a secondary substrate.

Methods for introducing oligonucleotide functionalizing reagents to introduce one or more sulfhydryl, amino or hydroxyl moieties into the oligonucleotide probe sequence, typically at the 5' terminus are described in U.S. Pat. No. 4,914,210. A 5' phosphate group can be introduced as a radioisotope by using polynucleotide kinase and $\gamma$-$^{32}P$-ATP to provide a reporter group. Biotin can be added to the 5' end by reacting an aminothymidine residue, introduced during synthesis, with an N-hydroxysuccinimide ester of biotin.

Oligonucleotide (DNA and RNA) derivatives are also available labels. For example, etheno-dA and etheno-A are known fluorescent adenine nucleotides which can be incorporated into an ribo- or chimeric oligonucleotide probe. Similarly, etheno-dC is another analog that could be used in probe synthesis. The probes containing such nucleotide derivatives may be hydrolyzed to release much more strongly fluorescent mononucleotides during PCR.

Template-dependent extension of the oligonucleotide primer(s) is catalyzed by a polymerizing agent in the presence of adequate amounts of the four deoxyribonucleoside triphosphates (dATP, dGTP, dCTP, and dTTP) or analogs as discussed above, in a reaction medium which is comprised of the appropriate salts, metal cations and pH buffering system. Suitable polymerizing agents are enzymes known to catalyze primer and template-dependent DNA synthesis and possess the 5' to 3' nuclease activity. Known DNA polymerases include, for example, E. coli DNA polymerase I, Thermus thermophilus (Tth) DNA polymerase, Bacillus stearothermophilus DNA polymerase, Thermococcus littoralis DNA polymerase, and Thermus aquaticus (Taq) DNA polymerase. The reaction conditions for catalyzing DNA synthesis with these DNA polymerases are well known in the art. To be useful in the present invention, the RNase H must efficiently cleave the ribo- or chimeric oligonucleotide probe and release labeled fragments so that the signal is directly or indirectly generated.

The products of the synthesis are duplex molecules consisting of the template strands and the primer extension strands, which include the target sequence. By-products of this synthesis are labeled oligonucleotide fragments which consist of a mixture of mono-, di- and larger nucleotide fragments. Repeated cycles of denaturation, labeled probe and primer annealing, and primer extension and cleavage of the labeled probe result in the exponential accumulation of the target region defined by the primers and the exponential generation of labeled fragments. Sufficient cycles are run to achieve a detectable species of label, which is generally several orders of magnitude greater than background signal.

In a preferred method, the PCR reaction is carried out as an automated process which utilizes thermostable enzymes. In this process the reaction mixture is cycled through a denaturing step, a probe and primer annealing step, and a synthesis step, whereby cleavage and displacement occurs simultaneously with primer dependent template extension. A DNA thermal cycler, such as the commercially available machine from Perkin-Elmer/ABI Instruments, which is specifically designed for use with a thermostable enzyme, may be employed.

Temperature stable polymerases are preferred in this automated process because the preferred way of denaturing the double stranded extension products is by exposing them to a high temperature (about 95° C.) during the PCR cycle for example, U.S. Pat. No 4,889,818 discloses a representative thermostable enzyme isolated from Thermus aquaticus. Additional representative temperature stable polymerases include, e.g., polymerases extracted from the thermostable bacteria Thermus flavus, Thermus ruber, Thermus thermophilus, Bacillus stearothermophilus (which has a somewhat lower temperature optimum than the others listed), Thermus lacteus, Thermus rubens, Thermatoga maritima, Thermococcus littoralis, and Methanothermus fervidus.

Detection or verification of the labeled oligonucleotide fragments may be accomplished by a variety of methods and may be dependent on the source of the label or labels employed. One convenient embodiment of the invention is to subject the reaction products, including the cleaved label fragments to size analysis. Methods for determining the size of the labeled nucleic acid fragments are known in the art, and include, for example, gel electrophoresis, sedimentation in gradients, gel exclusion chromatography and homochromatography.

During or after amplification, separation of the labeled fragments from the PCR mixture can be accomplished by, for example, contacting the PCR mixture with a solid phase extractant (SPE) for example, materials having an ability to bind oligonucleotides on the basis of size, charge or interaction with the oligonucleotide bases can be added to the PCR mixture, under conditions where labeled, uncleaved oligonucleotides are bound and labeled fragments are not. Such SPE materials include ion exchange resins or beads, such as the commercially available binding particles Nensorb™ (DuPont Chemical Co.). Nucleogen™ (the Nest Group) and hyroxylapatite. In a specific embodiment, if a dual labeled probe comprising a 3' biotin label separated from a 5' label by a nuclease susceptible cleavage site is employed as the signal means, the PCR amplified mixture can be contacted with materials containing a specific binding partner such as avidin or streptavidin, or an antibody or monoclonal antibody to biotin. Such materials can include beads and particles coated with specific binding partner and can also include magnetic particles.

Following the step wherein the PCR mixture has been contacted with a SPE, the SPE material can be removed by filtration, sedimentation or magnetic attraction leaving the labeled fragments free of uncleaved labeled oligonucleotides and available for detection.

Reagents employed in the methods of the invention can be packaged into diagnostic kits. Diagnostic kits include the labeled oligonucleotides and the primers in separate containers. If the oligonucleotide is unlabeled, the specific labeling reagents may also be included in the kit. The kit may also contain other suitably packaged reagents and materials needed for amplification, for example, buffers, dNTPs, and/or polymerizing means, and for detection analysis, for example, enzymes and solid phase extractants, as well as instructions for conducting the assay.

EXAMPLES

Table 1 shows the oligonucleotide sequences of the PCR primers and the ribo-oligonucleotide probe used in this example. The primers were selected for amplification of a segment of the BETA-actin gene. The probe was labeled with 6-carboxyfluorescein (6-FAM) at the 5' end and 6-carboxytetramethylrhodamine (TAMRA) at the 3' end. The primers and probe were obtained as a custom synthesis from Perkin-Elmer.

Table 1. Primer and Probe Sequences

SEQ ID NO. 1:

Forward Primer: 5' CAC ACT GTC CCC ATC TA 3'

SEQ ID NO. 2:

Reverse Primer: 5' GGA ACC GCT CAT TG 3'

SEQ ID NO. 3:

Probe sequence: 5' AUG CCC CCC CCA UGC CAU CCU GCG U 3'

The PCR amplification was performed using a GeneAmp PCR System (Perkin-Elmer) using 50 µl reactions that contained 1X Bicine buffer (Perkin-Elmer), 2.5 mM Mn(OAc)$_2$, 200 µM dNTP's (Perkin-Elmer), 0–16 Units of thermostable RNase H (Epicentre Technologies), 1.25 Units of Δ Tth DNA Polymerase (Clonetech), human male DNA (Perkin-Elmer), 400 nM of each primer and 50 nM of labeled probe. The thermal regimen was 95° C. for 2 min, and then 40 cycles of 60° C. for 20 sec, 45° C. for 1 min and 95° for 15 sec. FAM fluorescence was measured using a Taq-Man LS-50B System (Perkin-Elmer).

FIG. 1 shows the FAM fluorescence detected real time during PCR cycling. Curve 1 represents the baseline fluorescence obtained with no RNase H added to the reaction and thus no release of label. Curves 2–5 represent the addition of 1, 2, 4 and 16 Units of RNase H to the reaction, respectively. Amplification of the BETA-actin gene segment is reflected by the real time increase in fluorescence, directly dependent on the amount of RNase H available to cleave the probe and release the label.

The invention has been described with a particular view to the presently preferred embodiments. However, it will be obvious that certain changes and modifications may be practiced within the scope of the invention by those of skill in the art.

SEQUENCE LISTING ( 1 ) GENERAL INFORMATION:

( i i i ) NUMBER OF SEQUENCES: 3

( 2 ) INFORMATION FOR SEQ ID NO:1:

-continued ( i ) SEQUENCE CHARACTERISTICS:
    ( A ) LENGTH: 17
    ( B ) TYPE: NUCLEIC ACID
    ( C ) STRANDEDNESS: SINGLE
    ( D ) TOPOLOGY: LINEAR ( i i ) MOLECULE TYPE: DNA ( x i ) SEQUENCE DESCRIPTION: SEQ ID NO:1:

CAC ACT GTC CCC ATC TA 17

( 2 ) INFORMATION FOR SEQ ID NO:2:

( i ) SEQUENCE CHARACTERISTICS:
    ( A ) LENGTH: 14
    ( B ) TYPE: NUCLEIC ACID
    ( C ) STRANDEDNESS: SINGLE
    ( D ) TOPOLOGY: LINEAR ( i i ) MOLECULE TYPE: DNA ( x i ) SEQUENCE DESCRIPTION: SEQ ID NO:2:

GGA ACC GCT CAT TG 14

( 2 ) INFORMATION FOR SEQ ID NO:3:

( i ) SEQUENCE CHARACTERISTICS:
    ( A ) LENGTH: 26
    ( B ) TYPE: NUCLEIC ACID
    ( C ) STRANDEDNESS: SINGLE
    ( D ) TOPOLOGY: LINEAR ( i i ) MOLECULE TYPE: RNA ( x i ) SEQUENCE DESCRIPTION: SEQ ID NO:3:

AUG CCC CCC CCA YGC CAU CCU GCGT U 26

What is claimed is:

1. A method for the detection of a target DNA sequence in a sample comprising the steps of:

a) contacting and annealing a probe comprising a ribo-oligonucleotide attached to a first label with a sample containing a target single-stranded DNA sequence having a region complementary to the probe;

b) cleaving at least one of the ribonucleotides of the annealed probe with a ribo-nucleic acid nuclease capable of hydrolyzing ribonucleotides in a double stranded RNA:DNA duplex to release labeled ribo-oligonucleotide fragments; and c) generating a signal from the released labeled ribo-oligonucleotide fragments that kinetically characterizes the target DNA sequence; wherein steps a)–c) are performed in a single reaction mixture.

2. The method of claim 1, wherein the step of contacting and annealing a probe comprises contacting and annealing a chimeric oligonucleotide.

3. The method of claim 2, wherein the step of contacting and annealing a probe comprises contacting and annealing a chimeric RNA:DNA:RNA oligonucleotide.

4. The method of claim 1, further comprising the ribo-oligonucleotide attached to a second label wherein the first and second labels comprise interactive signal-generating moieties such that attachment of the labels causes the second label to suppress detection of the first label.

5. The method of claim 4, wherein the first label comprises a reporter fluorescent dye and the second label comprises a quencher fluorescent dye and wherein the step of measuring the release of labeled ribo-oligonucleotide fragments comprises detecting reporter fluorescence.

6. The method of claim 5, wherein the reporter and the quencher are separated by less than about 10 nucleotides.

7. The method of claim 5, wherein the probe has a secondary structure that brings the reporter and quencher into close proximity prior to the step of annealing the probe to the target DNA sequence.

* * * * *